United States Patent [19]

Hall

[11] 4,195,126

[45] Mar. 25, 1980

[54] ALBUMIN-DYE COMPLEX FOR FATTY ACID DETERMINATION

[75] Inventor: Leo M. Hall, Homewood, Ala.

[73] Assignee: The Board of Trustees of the University of Alabama, Birmingham, Ala.

[21] Appl. No.: 839,361

[22] Filed: Oct. 4, 1977

[51] Int. Cl.$^2$ .................... G01N 31/14; G01N 33/16; C07G 7/00

[52] U.S. Cl. ..................... 435/11; 23/230 B; 23/902; 23/909; 260/121; 424/2; 435/18; 435/19

[58] Field of Search ............ 195/99, 103.5 R; 23/230 B, 231, 902, 909; 260/121, 122; 424/2

[56] References Cited

U.S. PATENT DOCUMENTS

| | | | |
|---|---|---|---|
| 3,703,591 | 11/1972 | Bucolo et al. | 195/103.5 R |
| 3,751,381 | 8/1973 | Megram | 23/909 X |
| 3,983,005 | 9/1976 | Goodhue et al. | 195/103.5 R |
| 4,038,146 | 7/1977 | Nonatz et al. | 195/103.5 R |
| 4,043,997 | 8/1977 | Schroeder | 260/122 |
| 4,066,508 | 1/1978 | Ranscher et al. | 195/103.5 R X |
| 4,093,612 | 6/1978 | Travis et al. | 260/121 X |

OTHER PUBLICATIONS

Irving et al., The Binding of Organic Ions by Proteins, J. Amer. Chem. Soc., vol. 68, 1946, (pp. 1486-1490).
Irving, M. K., Spectrophotometric Investigations of the Interactions of Proteins with Organic Anions, J. Amer. Chem. Soc., vol. 68, 1946, (pp. 2299-2304).
Daniel et al., Cooperative Effects in Binding by Bovine Serum Albumin, Biochemistry, vol. 5, No. 6, 1966, (pp. 1893-1900).

Primary Examiner—David M. Naff
Attorney, Agent, or Firm—Oblon, Fisher, Spivak, McClelland & Maier

[57] ABSTRACT

An albumin-dye complex is prepared containing serum or plasma albumin which is substantially free of endogenous fatty acids and which has been complexed with a fatty acid and dye which dye may be displaced from the albumin-dye complex by free fatty acids. The complex is used to quantitatively determine fatty acids, compounds which hydrolyze to fatty acids or activity of hydrolase enzymes that produce fatty acids from a substrate.

36 Claims, 5 Drawing Figures

ALBUMIN-DYE COMPLEX FOR FATTY ACID DETERMINATION

BACKGROUND OF THE INVENTION

1. Field of the Invention

The present invention relates to albumin-dye complexes and the quantitative determination of free fatty acids, compounds which upon hydrolysis yield fatty acids in aqueous systems, or in determination of the activity of hydrolase enzymes which will act on appropriate substrates to produce fatty acids.

2. Description of the Prior Art

It is known that albumin can bind a number of ligands, including dyestuffs, see for instance the disclosure by Oscar Bally in U.S. Pat. No. 1,543,543 and by Saturo Honio et al, in U.S. Pat. No. 3,679,586, Klotz et al in the *Journal of the American Chemical Society, volume* 68, 1946, pages 1486-1490, discuss the binding of organic ions by albumin. Klotz, in the *Journal of the American Chemical Society*, volume 68, 1946, pages 2299-2304, and Daniel and Weber, *Biochem*, 5:1893 (196) have demonstrated that spectral shifts and/or absorbance or flourescence changes accompany the interaction of albumin with an organic dye and that these changes could be partially reversed upon the addition of competing ligands.

Previous methods for the determination of fatty acids in aqueous samples include three principal techniques:

(1) Titration of the fatty acids with alkali, V. P. Dole, *Journal of Clinical Investigation*, 35:150 (1956).

(2) Determination as the copper salt after extraction with a suitable solvent, W. G. Duncombe, *Biochemical Journal*, 88:7 (1963), and (3) Chromatographic procedures.

These techniques are time consuming and, in general, not adaptable to rapid, automated analysis techniques.

In addition to determining the free fatty acid content in aqueous samples, such as blood serum and milk, it has become desirable to determine the quantity of triglycerides, cholesterol esters and phospholipids present. It is of particular interest to analyze blood serum for both triglyceride and cholesterol content since excessive levels of these substances in the blood serum have been linked with a variety of cardiovascular problems. K. A. Slickers in *Lab World*, volume 27, pages 8-14 (1976), summarizes the enzymatic methods of determining the triglyceride content. In general, these techniques involve either the saponification of the triglyceride to glycerol with alkali hydroxide or its hydrolysis by a triacylglycerol hydrolase enzyme to free glycerol. The glycerol content then being determined by an appropriate technique. Komatsu in U.S. Pat. No. 3,898,130, describes an enzymatic hydrolysis process for triglycerides. Wahlfeld et al in U.S. Pat. No. 3,862,009 and Bucolo et al in U.S. Pat. No. 3,703,591 disclose integrated triglyceride determination processes. In this process, the triglyceride is enzymatically hydrolyzed to glycerol and the glycerol content determined spectrophotometrically by measuring the change in adsorption of the solution. In order to accomplish this, it was necessary for both Wahlfeld et al and Bucolo et al to include in their system adenosine triphosphate (ATP), glycerokinase (GK), phosphenol pyruvate (PEP), lactate dehydrogenase (LDH) and reduced nicotinamide-adenine-dinucleotide (NADH). The absorbance of this solution changes as NADH is oxidized to NAD as the end result of several enzymatic reactions.

In order to determine the quantity of cholesterol in a sample it is necessary to first hydrolyze any cholesterol esters to cholesterol. There are two basic techniques for accomplishing this. One is alcoholic saponification with an alkali hydroxide, such as KOH, and the other is enzymatic hydrolysis. The amount of total cholesterol may then be determined by a variety of techniques. E. V. Cardinal suggested in U.S. Pat. No. 3,479,154, precipitation of the cholesterol with known quantity of digitonin, separation of the precipitate, followed by analysis for digitonin.

Recently several integrated enzymatic processes for cholesterol determination have been proposed. Goodhue et al in U.S. Pat. No. 3,884,764, suggest enzymatically hydrolyzing the cholesterol ester with a combination of a lipase having cholesterol esterase activity, a protease and cholesterol oxidase whereby the cholesterol is converted to free cholesterol which is enzymatically oxidized. The quantity is then determined by measuring the quantity of one of the products of the cholesterol oxidation. The measurement may be conducted by enzymatic techniques if desired.

Methods for the determination of phospholipids, such as lecithin, sphingomyelin, cerebrosides, and gangliosides have proven unsatisfactory. Lecithin has been determined by procedures based upon selective extraction into appropriate organic solvents followed by chemical determination of organic soluble phosphorus. Chromatographic procedures have also been employed to isolate the lecithin fraction from interfering substances followed by chemical detection methods. The use of the enzymes phospholipase $A_2$ and phospholipase D in the analysis for lecithin has been reported. Analytical methods for the determination of sphingomyelin, cerebrosides and gangliosides involve extraction, chromatographic separations to remove interfering substances, and the application of chemical detection methods. These techniques involve a number of processing steps which make such determinations time consuming and costly.

Accordingly, there exists a need for a technique which is capable of quantitatively and qualitatively analyzing aqueous media for free fatty acids and compounds which may be hydrolyzed to free fatty acids such as triglycerides, cholesterol esters and phospholipids in a simple manner. In particular, for a technique which allows the determination of the components by direct spectrophotometric or fluorometric means.

SUMMARY OF THE INVENTION

It is an object of the present invention to provide a simple technique for the quantitative analysis of aqueous media containing a fatty acid or derivative thereof.

Another object of the present invention is to provide a direct spectrophotometric or fluorometric technique for quantitatively analyzing aqueous media which contain fatty acids or derivatives thereof.

It is further object of the present invention to provide a reagent composition for the direct spectrophotometric or fluorometric determination of compounds which upon hydrolysis by specific hydrolase enzymes produce fatty acids.

Yet another object of the present invention is to provide a direct spectrophotometric or fluorometric technique for qualitatively and quantitatively analyzing hydrolase enzymes which catalyze the hydrolysis of fatty acid derivatives.

Still another object of the present invention is to provide a reagent composition for the direct spectrophotometric or fluorometric quantitative analysis of hydrolase enzymes which catalyze the hydrolysis of esters or amides of fatty acids.

These and other objects of the present invention have been accomplished through the use of a reagent which comprises a dye-albumin complex which is substantially free of endogenous fatty acids and which has been pretreated with fatty acid. To determine the unesterified fatty acid content of an aqueous medium, one need only add this reagent to the medium and measure the change in the absorbance of the mixture. The interaction of the fatty acids in the aqueous medium with the albumin-dye complex displaces a portion of the dye from the complex which results in a change in the absorbance of the medium which is proportional to its fatty acid content. When it is desired to quantitatively analyze an aqueous medium for compounds which upon hydrolysis produce fatty acids, the change in the absorbance or fluorescence is measured before and after subjecting the medium to hydrolysis conditions. To analyze a sample for hydrolase enzyme activity, the dye-albumin complex and a suitable substrate which is hydrolyzed to a fatty acid by the enzyme in question, is added to an aqueous medium which contains the sample. The rate of change of the absorbance of the mixture is proportional to the hydrolase enzyme activity to the sample.

DETAILED DESCRIPTION OF THE PREFERRED EMBODIMENTS

Albumin of serum or plasma origin may be used in the albumin-dye complex of the present invention. The serum or plastma albumin may be prepared by a variety of methods; e.g. solvent fractionation described by Cohen et al in *JACS* 68:459 (1946) to give Fraction V; Sephadex$^R$ gel filtration as described by Killander, *Biochem. Biophys. Acta.* 93, 1 (1964) or by affinity chromatography as described by Easterday and Easterday in "Immobilized Biochemicals and Affinity Chromatography", Dunlap, ed., Plenum Publishing Corp., New York 1976 p. 123. However, serum or plasma itself may be used as a source of albumin if the serum or plasma is first delipidated by a procedure such as that described by Cham and Knowles, *J. Lipid Res.*, 17, 176 (1976).

The serum or plasma albumin may be of mammalian, avian reptillian or fish origin and includes albumin derived from rat, equine, canine, bovine, ovine, chicken, goat, human, rabbit, monkey, ape, chimpanzee and like sources. The preferred albumins are those of canine, bovine, porcine, and human origin. Bovine serum albumin, Fraction V, because of its ready availability, low cost, and binding affinity is most preferred. The serum or plasma albumin should be substantially free of endogenous fatty acid. The plasma or serum albumin is considered substantially free of endogenous fatty acid when less than 2 moles of endogenous fatty acid are present per mole of albumin. The represents about 20% of the endogenous fatty acid present in albumin in serum or plasma. Pretreatment of the albumin may be necessary to remove endogenous bound fatty acids. Such treatments are well known in the art. For instance, D. S. Goodman in *Science*, volume 125, pages 1296–1297, 1957, discloses the use of extraction with an organic solvent to remove bound fatty acids from albumin and Cham and Knowles, *J. Lipid Res.*, 17, 176 (1976) disclose the use of organic solvents to delipidate serum or plasma. R. F. Chen discloses in *JBC*, volume 42, pages 173–181, 1966, removing bound fatty acids from albumin by treatment with charcoal, while Reynolds et al *Biochemistry* 7:1357 (1968) suggest ion exchange chromatography to remove the bound fatty acids. Any technique capable of removing bound fatty acids from albumin may be employed. However, the ion exchange technique is preferred.

In order to obtain a linear absorbance change when the dye-albumin complex is introduced into an aqueous media containing fatty acids, the albumin must be treated with a fatty acid either before or after the dye-albumin complex is formed to form a complex. However, it is more convenient to add the fatty acid after the dye-albumin complex is formed. The amount of fatty acid used in the treatment need only be sufficient such that the absorbance change upon the addition of the complex to the aqueous solution of the fatty acid whose concentration is to be determined, follows the Beer-Lambert law. In general, the amount of fatty acid used in this treatment ranges from 0.5 to 4.0 moles of fatty acid per mole of albumin, preferably from 0.75 to 3.5 moles of fatty acid per mole of albumin but most preferably from 1.0 to 3.0 moles of fatty acid per mole of albumin.

The fatty acid used to treat the albumin is not critical, but in general will contain at least 8 carbon atoms. Preferably the fatty acid contains from 8 to 24 carbon atoms exclusive of additional side chains or functional groups. The fatty acid may be saturated or unsaturated and may contain non-interfering functional groups such as hydroxyl, sulfonic acid, phenyl, and the like. Suitable fatty acids include myristic, palmitic, oleic, stearic, octanoic, lauric, ricinoleic arachidonic, linoleic, linolenic, palmitoleic, arachidic, 8-phenyl octanoic, lignoceric, transhexadecenoic, and elaidic acids as well as sodium lauryl sulfate. The fatty acid composition of the medium to be assayed will, in general, determine which fatty acid is preferred for treatment. From the viewpoints of availability and cost, myristic, palmitic, oleic, ricinoleic, and stearic acids are preferred. The treatment is carried out by simply admixirg the fatty acid (dissolved in a water miscible solvent such as methanol or ethanol or if the lithium salt of ricinoleic acid is used, dissolved in water) with an aqueous albumin-dye solution or an aqueous albumin solution either before or after the addition of the dye. The temperature at which this occurs is not critical and may range from 0° to 50° C., but is preferably 20° to 40° C.

The dye which is present in the albumin-dye complex is chosen such that it may be displaced from the complex by free fatty acids. The dye should be selected such that it is not significantly displaced from the dye-albumin complex by any of the common non-fatty acid components found in the media whose fatty acid or fatty acid derivative content is to be determined. Thus, when the fatty acid content of blood serum is to be determined, the dye must not be significantly displaced by such common serum constituents as billirubin and bile salts.

Preferably the dye should also be capable of absorbing light within the UV-visible range, preferably light having a wave length within the range of from 300 to 800 nm, more preferably from 400 to 700 nm, most preferably from 400 to 625 nm. The dye chosen must be soluble in water. It is desirable that the dye exhibit absorbance at the pH prevailing in the reagent. It it does not, then a buffer may be employed so that the necessary pH will be obtained or some other means of altering the pH is used.

It is preferred that the dye exhibit a molar absorptivity of from $10^2$ to $10^7$, preferably from $10^2$ to $10^6$ but more preferably from $10^2$ to $10^5$. Dyes having greater or lesser molar absorptivities may result in a reagent which may lack the desired degree of sensitivity. Since fatty acids exhibit an association constant with albumin (K association) which is equal to or greater than $10^8/M$ it is preferred that the dye exhibit an association constant with albumin which is less than $10^8/M$. If the association constant of the dye exceeds $10^8/M$, then the detection of fatty acids having an association constant lower than that of the dye will be less sensitive. In general, however, the dye should possess an association constant with albumin which is less than $10^8/M$. Considering the possibility that the medium containing the fatty acids may also contain other materials which may displace the dye, it is preferred that the dye have an association constant with the albumin which is greater than $10^3/M$ though dyes having lower values are suitable if such other materials are not present in the medium. Preferably the dye has an association constant within the range of from $10^3/M$ to $10^8/M$, still more preferably from $10^4/M$ to $10^8/M$. Suitable dyes include compounds from the following classes: Azo, sulphonphthalein, triphenylmethane, fluorescein, naphthalenesulfonic acids, phenoxazine, anthraquinones, tricarbocyanine, indigo and acridine. Typical dyes include:

Of these dyes sulfobromophthalein, resazurin, chlorophenol red, Orange III, bromophenol blue and dichlorofluorescein are preferred.

The complex is generally not recovered, but used as prepared. The solution containing the albumin-dye complex may be freeze dried and used after reconstitution with water.

For determining fatty acids by fluorometric techniques, the dye must be capable of exhibiting a change in fluorescence when it is complexed to albumin. The presence of fatty acid disturbs the albumin-dye complex reversing the change in fluorescence. The change in fluorescence caused by the presence of the fatty acid is proportional to the fatty acid concentration added to the reagent. For example the fluorescein dye when complexed with albumin exhibit decreased fluorescence which is reversed in the presence of fatty acids. Other characteristics of the fluorescent dyes are similar to those of dyes used in the spectrophotometric measurements. Indeed the fluorescent dyes can also be used for the spectrophotometric determination of fatty acids as described. The fluorometric technique differs only in the measurement technique employed and in the concentrations of albumin and fluorescent dye used. For the fluorometric technique reagents containing from $5\times10^{-7}$ M of albumin and $2\times10^{-6}$ M to $10^{-7}$ M dye are appropriate.

The concentration of the albumin and dye in the solution is not critical. In general, an albumin, concentration within the range of from $1.2\times10^{-4}$ M to $3.0\times10^{-5}$ M is suitable, with a dye/albumin molar ratio of from 0.16 to 8.8 being preferred. In general, aqueous solutions of the albumin-dye complex will also contain a buffer. The amount of buffer present is not critical. In general, buffer concentrations from 0.01 M to 1.0 M are suitable, preferably from 0.05 M to 0.25 M, more preferably from 0.10 M to 0.20 M.

The selection of the buffer when used for the various dye-albumin reagents is dictated by the pH at which the various dyes give light absorption in the visible spectrum. The buffer choice is also dependent upon other components of the complete reagent system in particular, when one or more enzymes are incorporated into the reagent. In this case, the buffer may be selected such that its $pK_a$ is in the region of maximal enzyme activity. It is not necessary, or even desirable, in certain in-

| Azo Dyes | Sulfonephthalein Dyes | Triphenylmethane Dyes |
|---|---|---|
| Amaranthum | Bromocresol Green | Coomassie Brilliant Blue[R] |
| Orange I | Bromocresol Purple | Crystal Violet |
| Orange III | Bromophenol Blue | Malachite Green |
| Orange IV | Bromothymol Blue | |
| Congo Red | Chlorophenol Red | Fluroescein Dyes |
| Evans Blue | Cresol Red | Dichlorofluorescein |
| Naphthol Blue Black | Metacresol Purple | Fluorescein |
| HABA | Sulfobromophthalein | Fluoresceinisothiocyanate |
| Ponceau 3 R | Thymol Blue | |
| Ponceau S | | |
| Azocarmine B | | |

| Phenoxazine Dyes | Naphthalenesulfonic acid Dyes | Indigo Dyes |
|---|---|---|
| Resazurin | Anilinonaphthalene sulfonic acid | Indigo Carmine |
| Brilliant Cresyl Blue | Naphthol Yellow S | |

| Acridine Dyes | Anthraquinone Dyes | Tricarbocyanine Dyes |
|---|---|---|
| Acriflavine | Alizarin Red S | Indocyanine Green |

The following compounds did not work: Nile Blue A, Sudan III, Sudan IV, Alcian Blue, Dichloroindophenol, Rhodamine 6 G.

stances, to select a buffer whose pH is adjusted to that pH at which maximum light absorption by the dye occurs since one is only interested in the change in absorption. Any buffer which is compatible with the system may be used. Suitable buffers include piperazine hydrochloride, and the anions of phosphoric, pyrophosphoric, cacodylic, dimethylglutaric, succinic, citric, acetic and boric acids. The particular cation employed is not critical so long as it does not form an insoluble precipitate with the dye or other components of the system. The sodium, lithium and ammonium salts of the anion are preferred since the use of potassium salts can lead to the formation of insoluble salts of the dyes in some instances.

The albumin-dye reagent of the present invention can be used to determine the fatty acid content of essentially any aqueous medium containing fatty acids of chain length greater than $C_{10}$ such as blood serum or plasma, cerebrospinal fluid, urine, synovial fluid, amniotic fluid and the like. If the fatty acids are present in the form of esters or amides it is necessary to first saponify the sample to produce the free fatty acid. Such saponification techniques are well known, for example the use of alcoholic KOH is one common technique. The use of such saponification techniques result in the analysis being non-specific since the media may contain several compounds which release fatty acids upon hydrolysis. If it is desired to determine the concentration of a particular compound which releases fatty acids upon hydrolysis, then the hydrolysis should be conducted enzymatically using a hydrolase enzyme specific for the compound in question. Many such enzymes are known. This embodiment is particularly useful in the quantitative and qualitative analysis of complex aqueous media such as blood serum or plasma, cerebrospinal fluid, urine, synovial fluid, amniotic fluid and the like.

This technique may also be employed to analyze for compounds which do not produce fatty acids upon enzymatic hydrolysis if the compounds can be enzymatically treated to yield a product which does yield fatty acids upon hydrolysis. Thus, it is possible to analyze blood serum for sphingomyelin, cerbrosides and glangliosides even though these compounds do not produce fatty acids directly since each of these components may be treated with an appropriate enzyme to produce ceramide which does, upon hydrolysis, produce fatty acids.

The albumin-dye reagent is particularly useful in analyzing blood serum for many of its constituents, such as triglycerides, cholesterol esters, and phospholipids such as lecithin, ceramides, sphingomyelin, cerebrosides and gangliosides. Blood serum or plasma may be directly analyzed for triglycerides, cholesterol esters, lecithin and ceramides by simply introducing the serum or plasma into the dye-albumin reagent containing the appropriate hydrolase enzyme. When analyzing for triglycerides the hydrolase enzyme employed is preferably derived from *Chromobacterium viscosum, Geotrichum candidum, Rhizopus arrhizus, Rhizopus delamar,* and hog pancreas. Preferably the hydrolase derived from *Rhizopus arrhizus* or from *Rhizopus delamar* is used because of greater specificity of triglycerides. Hydrolase enzymes suitable for cholesterol esters include cholesterol esterase derived from bovine or hog pancreas. Hydrolase enzymes used with lecithin include phospholipase A derived from a variety of venom including *Vipera russelli, Crotalus adamanthus, Crotalus terrificus terrificus, Naja naja* or bee venom. The hydrolase enzymes which may be employed to hydrolyze ceramides include ceramidase.

When analyzing for sphingomeylin, cerebrosides or gangliosides it is necessary to first enzymatically hydrolyze these components to ceramide. The ceramide is then enzymatically hydrolyzed to produce fatty acids which displace the dye from dye-albumin complex and the change in absorbance is measured. Enzymes suitable for converting sphingomyelin, cerebrosides and gangliosides into ceramide are well known and include sphingomyelinase for sphingomyelin, $\beta$-glucuronidase for the cerebrosides; and $\beta$-glucosidase, $\beta$-galactosidase, sialadase and $\beta$-N-cetylhexosaminadase for gangliosides.

Some of the various reactions involved in the analysis of blood serum are:

A. For triglycerides:

Fatty acids + Albumin-Dye-Complex ⟶ Albumin-Fatty acid-Complex + Dye

B. For Cholesterol esters:

Fatty acids + Albumin-Dye Complex ⟶ Albumin-Fatty acid-Complex + Dye

C. For lecithin:

Fatty acids + Albumin-Dye-Complex ⟶ Albumin-Fatty acid-Complex + Dye

D. For ceramides:

Fatty acids + Albumin-Dye-Complex ⟶ Albumin-Fatty acid-Complex + Dye

E. For sphingomyelin:

Fatty acids + Albumin-Dye-Complex ⟶ Albumin-Fatty acid-Complex + Dye

F. For cerebrosides:

G. For gangliosides:

In conducting the analysis of aqueous samples which contain components which yield fatty acids upon hydrolysis, one simply measures the absorbance of the reagent containing sample and then measures the absorbance other hydrolysis of the component, preferably in enzymatic hydrolysis. The absorbance change is proportional to the concentration of the component in the sample. By reference to the absorbance change caused by a known quantity of fatty acid introduced into a separate reagent, the concentration of liberated fatty acid can be readily calculated by simple proportion. Alternatively two equal aliquots of the sample are taken and one is hydrolyzed. Reagent is added to both and the difference in absorbance of the two mixtures is determined. This procedure is especially useful if the optimum pH of the hydrolase enzyme is different from that of the reagent itself. In such a case, the buffering capacity of the reagent is made sufficient to counteract the pH difference between the reagent and the hydrolysis mixture. Calculation of the content of the component in the sample is as previously described. A preferred method of analysis when large numbers of samples are to be analyzed is to employ a continuous flow analyzer such as that manufactured by Technicon ®. In such a system a dual channel colorimeter is utilized. The sample to be analyzed to split into two aliquots which are introduced, respectively, into two reagent streams, one of which contains the albumin-dye complex with the appropriate hydrolase enzyme and the other of which contains only the albumin-dye complex. Dialyzers in each of the reagent streams may be employed as required. With suitable incubation time the component to be analyzed is hydrolyzed and the difference in the absorbance of the two reagent streams is continuously monitored by the colorimeter. The difference in absorbance is proportional to the concentration of the component in the sample.

When it is desired to analyze for hydrolase enzymes, the procedure differs slightly. In this embodiment, the unknown suspected of containing a particular hydrolase enzyme is admixed with a reagent comprising the appropriate substrate, which is hydrolyzed by the enzyme, the albumin-dye reagent and a buffer. The rate of change of the absorbance of the mixture is proportional to the hydrolase activity in the sample. When measuring for hydrolase activity, any auxillary enzymes which may be necessary are added in excess so as to assure that the rate limiting step is the hydrolase activity. Using this technique it is possible to analyze for hydrolases such as ceramidase by adding ceramide and an albumin-dye sample; phospholiphase A by adding lecithin and an albumin-dye reagent; cholesterol esterase by adding cholesterol ester and an albumin-dye reagent; carboxylic ester hydrolase by adding triglyceride and an albumin-dye reagent.

Having generally described this invention, a further understanding can be obtained by reference to certain specific examples which are provided herein for purposes of illustration only and are not intended to be limiting unless otherwise specified.

EXAMPLE 1

Preparation of the Albumin-Dye Complex Reagent

Bovine serum albumin Fraction V was treated to remove endogenous fatty acids according to the procedure of Reynolds et al, *Biochemistry* 7 1357 (1968) and lyophillized.

Figure 1:
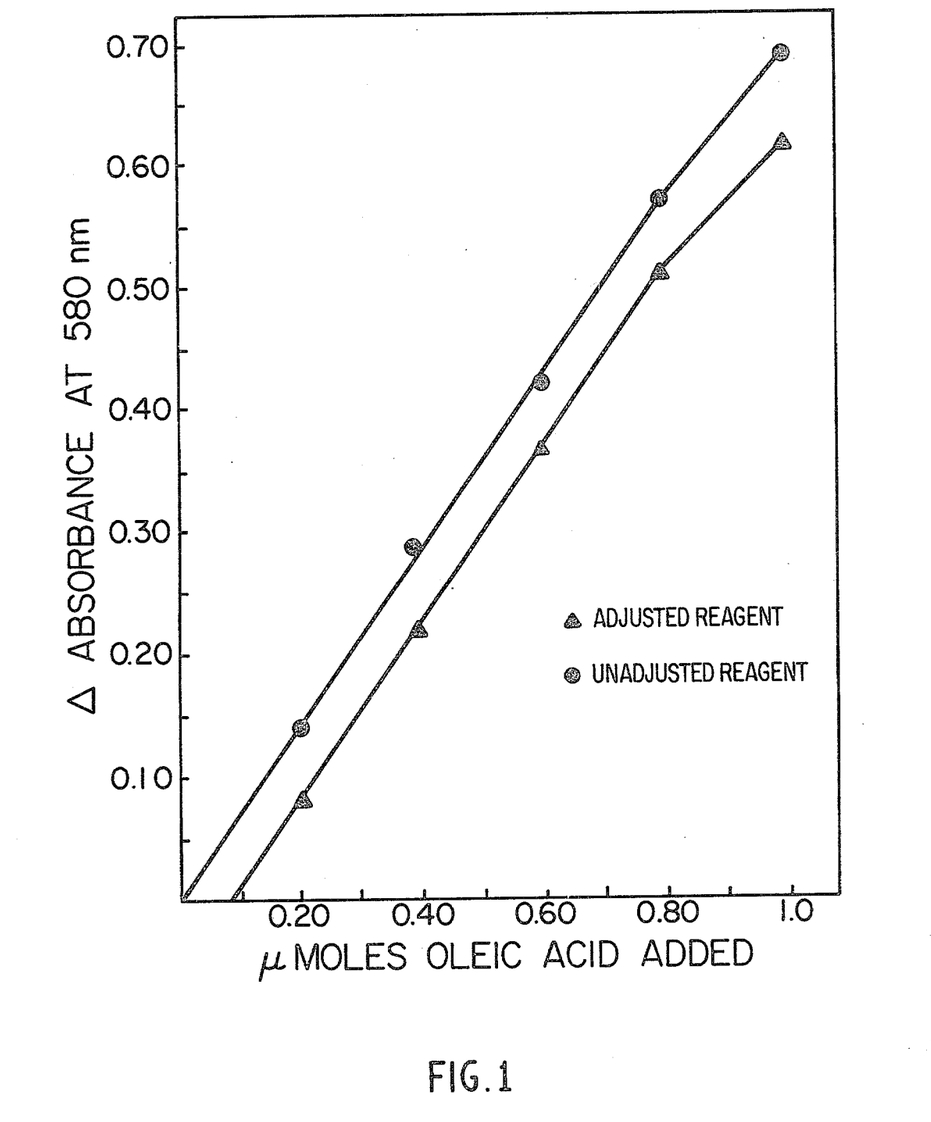
FIG. 1 illustrates the response of adjusted and unadjusted albumin-dye complex reagent to the addition of oleic acid.

To 800 ml of deionized water 27.6 gm of $NaH_2PO_4$ were added and the pH was adjusted to $7.8\pm0.05$ with NaOH. At room temperature, 3.45 gm of the treated bovine serum albumin were dissolved with gentle stirring. 200 mg of sulfobromophthalein were added and stirred to dissolve. As a preservative, (optional) 2.0 gm of sodium azide were added to the solution, and the volume was adjusted to 1000 ml. To obtain a linear response of absorbance change upon addition of known amounts of fatty acid, it was necessary to adjust the response of the reagent with a fatty acid. The adjustment was made by the addition of 7.0 ml of 0.02 M oleic acid dissolved in methanol. As shown in FIG. 1, the response of the reagent prior to the addition of the oleic acid results in a regression line with a negative intercept. However, after the addition of oleic acid the regression line passes through the origin and follows the Beer-lambert law over a sufficient concentration range of exogenous fatty acid to permit measurement of fatty acids or fatty acid derivatives in samples of biological origin.

FIG. 1. The response of the adjusted and unadjusted albumin-dye complex reagent to the addition of oleic acid. 50 $\mu l$ aliquots of methanolic solutions of oleic acid were added to 3.0 ml of reagents in spectrophotometer cells. The absorbance was measured before and after the addition of fatty acid and compared with the absorbance of a reagent to which only methanol was added. Measurements were at 37° C. at 580 nm.

EXAMPLE 2

Suitability of Proteins from Various Sources as a Component of the Albumin-Dye Complex Reagent Reagent formulations were prepared by dissolving the proteins as specified in Table 1, and sulfobromophthalein, 0.200 mg/ml, in potassium phosphate buffer, 0.30 M, pH 7.8. The initial absorbance of each solution was determined. The change in absorbance caused by the addition of 1.00 $\mu mol$ of oleic acid to a 3.00 ml volume of reagent was subsequently determined. Temperature was 37° C. Wavelength of measurement was 580 nm. As shown in Table 1, only albumins of serum or plasma origin are suitable as a component of the reagent, since the addition of oleic acid caused displacement of dye only in those reagents containing albumin as indicated by an increased absorbance upon the addition of oleic acid. The albumin used may be prepared by solvent fractionation, Sephadex ® gel filtration, or by affinity chromatography. Also shown in Table 1 is the suitability of delipidated serum or plasma as a source of albumin without further purification. Albumins which are not derived from plasma or serum such as lactalbumin or ovalbumin are not suitable as a component of the reagent since the addition of oleic acid did not result in an increased absorbance in reagents containing these proteins. Other proteins of serum such as gamma or beta globulins are not suitable.

TABLE 1

Response of Reagents Containing Sulfobromophthalein and Various Proteins to the Addition of Oleic Acid

| Source of Protein | Change in Absorbance upon Addition of Oleic Acid |
|---|---|
| Albumin, Fraction V[1] | |
| Rat | +0.424 |
| Equine | +0.430 |
| Canine | +0.828 |
| Bovine | +0.450 |
| Ovine | +0.426 |
| Porcine | +0.590 |
| Chicken | +0.286 |
| Goat | +0.584 |
| Human | +0.824 |
| Rabbit | +0.484 |
| Serum, delipidated, Human[2] | +0.859 |
| Serum, delipidated, Bovine[2] | +0.447 |
| Albumin, Sephadex G-100$^R$ fraction, Human plasma[3] | +0.747 |
| Albumin, Sephadex G-100$^R$ fraction, Bovine serum[3] | +0.387 |
| Albumin, Blue Sepharose CL-6B$^R$ fraction, Human Serum[4] | +1.02 |
| Albumin, Blue Sehparose Cl-6B$^R$ fraction, Bovine Serum[4] | +0.343 |
| Gamma globulin, Fraction II, Bovine[1] | −0.015 |
| Beta globulin, Fraction III, Bovine[1] | +0.022 |
| Lactalbumin, Milk[5] | −0.120 |
| Ovalbumin, Egg[5] | −0.050 |

[1]Bovine serum fractions II, III, and V, prepared according to Cohen et al, JACS, 68, 459–475 (1946), were used at a concentration of 3.45 mg/ml.
[2]Serum was delipidated according to Cham and Knowles, J. Lipid Res., 17, 176–181 (1976) and lyophilized. The lyophilized preparation was used at a concentration of 5.66 mg/ml.
[3]The albumin fraction of delipidated serum was prepared by gel filtration and lyophilized. (Killander, Biochem. Biophys. Acta 93, 1–14 (1964)). The lyophilized preparation was used at a concentration of 3.45 mg/ml.
[4]The albumin fraction of delipidated serum was prepared by affinity chromatography and lyophilized. (Easterday and Easterday in "Immobilized Biochemicals and Affinity Chromatography" Dunlap, ed., Plenum Publishing Corp., New York, 1976, p. 123–133). The lyophilized preparation was used at a concentration of 3.45 mg/ml.
[5]Concentration, 3.45 mg/ml.

EXAMPLE 3

Suitability of Various Dyes as a Component of the Albumin-Dye Complex Reagent

Amounts of various dyes were dissolved in 0.200 M potassium phosphate buffer, pH 7.8, containing 3.40 mg/ml of bovine serum albumin (Fraction V) such that the absorbance of the solution at 580 nm was between 0.30 and 1.5. Differential absorption spectra were measured using the solution as reference versus the same solution to which 1.00 μmol of oleic acid per 3.00 ml was added. A suitable dye is defined as one which demonstrated a change in absorbance in the presence of oleic acid of at least 0.04 absorbance. The wavelength of maximum response and the concentration of dye used was dependent upon the nature of the dye. Absorbance changes were either positive or negative with respect to the reagent containing no oleic acid. Although both can be used to measure the concentration of fatty acid, for technical reasons selection of a wave length at which positive absorbance change is observed is preferable.

TABLE 2

Suitability of Various Dyes as a Component of the Albumin-Dye Complex Reagent

| DYE | Concentration M × 10$^{-5}$ | Wave Length[1] | Response Δ Absorbance |
|---|---|---|---|
| Amaranthum | 6.1 | 585 | −.12 |
|  |  | 505 | +.22 |
| Orange I | 1.8 | 470 | +.12 |
| Orange III | 4.4 | 485 | +.21 |
|  |  | 410 | −.05 |
| Orange IV | 9.3 | 470 | +.30 |
|  |  | 360 | +.05 |
| HABA | 2.8 | 340 | +.11 |
| Congo Red | 5.0 | 460 | −.07 |
|  |  | 540 | −.08 |
|  |  | 470 | +.11 |
| Evans Blue | 1.8 | 645 | +.04 |
| Naphthol Blue Black | 5.3 | 570 | +.18 |
|  |  | 650 | −.13 |
| Cresol Red | 3.1 | 570 | +.16 |
| Sulfobromophthalein | 25 | 580 | +.45 |
| Bromothymol Blue | 1.7 | 435 | +.04 |
|  |  | 555 | −.04 |
| Bromophenol Blue | 1.7 | 585 | +.64 |
|  |  | 625 | −.52 |
| Bromocresol Green | 1.5 | 615 | +.13 |
|  |  | 670 | −.03 |
| Chlorophenol Red | 1.7 | 570 | +.32 |
|  |  | 600 | −.24 |
| Metacresol Purple | 8.4 | 435 | +.12 |
|  |  | 585 | +.08 |
| Bromocresol Purple | 2.2 | 615 | −.17 |
|  |  | 580 | +.16 |
| Thymol Blue | 9.1 | 480 | +.11 |
|  |  | 370 | +.03 |
| Brilliant Cresyl Blue | 10 | 600 | +.13 |
| Malachite Green | 1.7 | 620 | +.13 |
| Coomassie Brilliant Blue | 3.7 | 550 | +.10 |
| Crystal Violet | 1.7 | 525 | +.10 |
|  |  | 595 | −.13 |

TABLE 2-continued
Suitability of Various Dyes as a Component of the Albumin-Dye Complex Reagent

| DYE | Concentration M × 10$^{-5}$ | Wave Length[1] | Response Δ Absorbance |
|---|---|---|---|
| Ponceau S | 3.3 | 500 | +.18 |
|  |  | 565 | −.12 |
| Ponceau 3R | 3.2 | 495 | +.08 |
| Fluoresceinisothiocyanate | 1.8 | 485 | +.11 |
|  |  | 505 | −.16 |
| Dichlorofluorescein | 0.83 | 500 | +.27 |
|  |  | 520 | −.49 |
| Fluorescein | 0.84 | 485 | +.14 |
|  |  | 510 | −.20 |
| Naphthol Yellow S | 9.4 | 430 | +.10 |
|  |  | 460 | −.04 |
| Anilinonaphthalenesulfonate | 0.88 | 335 | +.07 |
|  |  | 385 | −.10 |
| Alizarin Red S | 10 | 460 | +.07 |
|  |  | 320 | +.08 |
| Resazurin | 45 | 585 | +.26 |
|  |  | 630 | −.50 |
| Indocyanine Green | 4.4 | 800 | +.55 |
| Acriflavine | 4.4 | 470 | +.13 |
| Indigo | 9.0 | 600 | +.14 |
| Azocarmine B | 5.0 | 490 | +.04 |

[1]The wavelengths listed are those at which maximum absorbance changes were observed. Absorbance changes are indicated as positive or negative with respect to the reference reagent containing no oleic acid.

EXAMPLE 4

Figure 2:
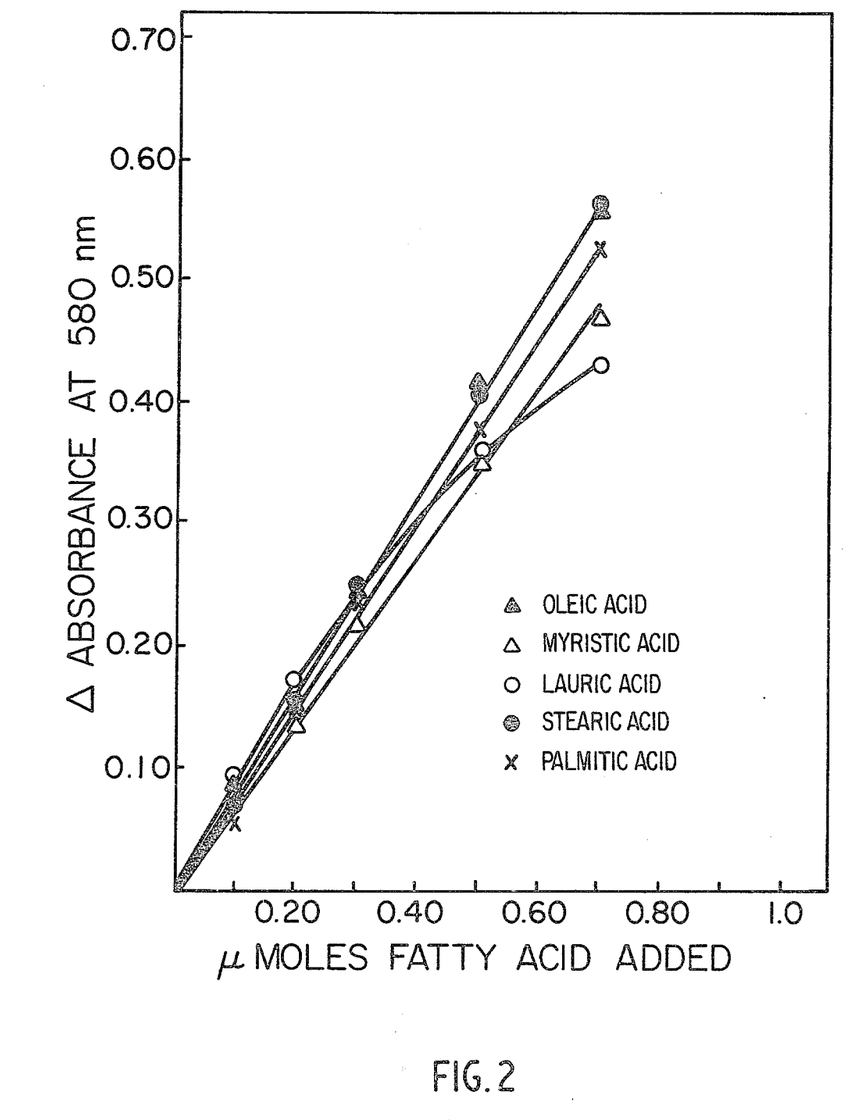
FIG. 2 illustrates the response of the albumin-dye reagent to the addition of various naturally occurring fatty acids.

Response of the Albumin-Dye Complex Reagent to the Addition of Various Naturally Occuring Fatty Acids The albumin-dye complex reagent was prepared by dissolving bovine serum albumin, defatted by the charcoal method of Chen, R. F.; JBC 242, 173 (1967), 2.77 mg/ml, and sulfobromophthalein 0.200 mg/ml, in 0.200 M potassium phosphate buffer, pH 7.8. The reagent was adjusted to yield a zero intercept by the addition of 0.04 μmoles/ml of oleic acid. To 3.00 ml of the adjusted reagent at 37.5° C., 50 μl aliquots of methanolic solution of the fatty acids were added and the increase in absorbance at 580 nm was determined. As shown in FIG. 2 the absorbance change upon the addition of oleic, palmitic, stearic, and myristic acids is essentially linear over the range of concentrations used. A slightly non-linear response is evident with lauric acid.

Given the fatty acid composition of naturally occuring lipids, only slight differences in the response of the reagent will be observed even with relatively large differences in the fatty acid components of lipids derived from natural sources.

EXAMPLE 5

Analysis of Triolein Added to Albumin-Dye Complex Reagent by Hydrolysis with Triacylglycerol Hydrolase of *Rhizopus arrhizus*

50 μl aliquots of isopropanol solutions of triolein were added to 3.0 ml of albumin-dye complex reagent (see Example 1) and 400 units of lipase from *Rhizopus arrhizus* were added. After incubation at 37° C. for 20 minutes the absorbance of each solution was determined and compared to that of 3.0 ml of the reagent to which 50 μl of isopropanol and 400 units of lipase were added. The change in absorbance at 580 nm was used to calculate the amount of fatty acid released upon hydrolysis, using a standard curve such as that presented in Example 1. The recovery of triolein was calculated on the basis of the known stoichiometry of hydrolysis of triolein to glycerol + 3 oleic acid. As shown in Table 3, the recovery of added triolein was essentially 100%.

TABLE 3

| | Analysis of Triolein | |
|---|---|---|
| Triolein added μ moles | Triolein measured μ moles | % Recovery |
| 0.0423 | 0.0411 | 97.1 |
| 0.0850 | 0.868 | 102 |
| 0.127 | 0.122 | 96.2 |
| 0.170 | 0.171 | 100 |

EXAMPLE 6

Figure 3:
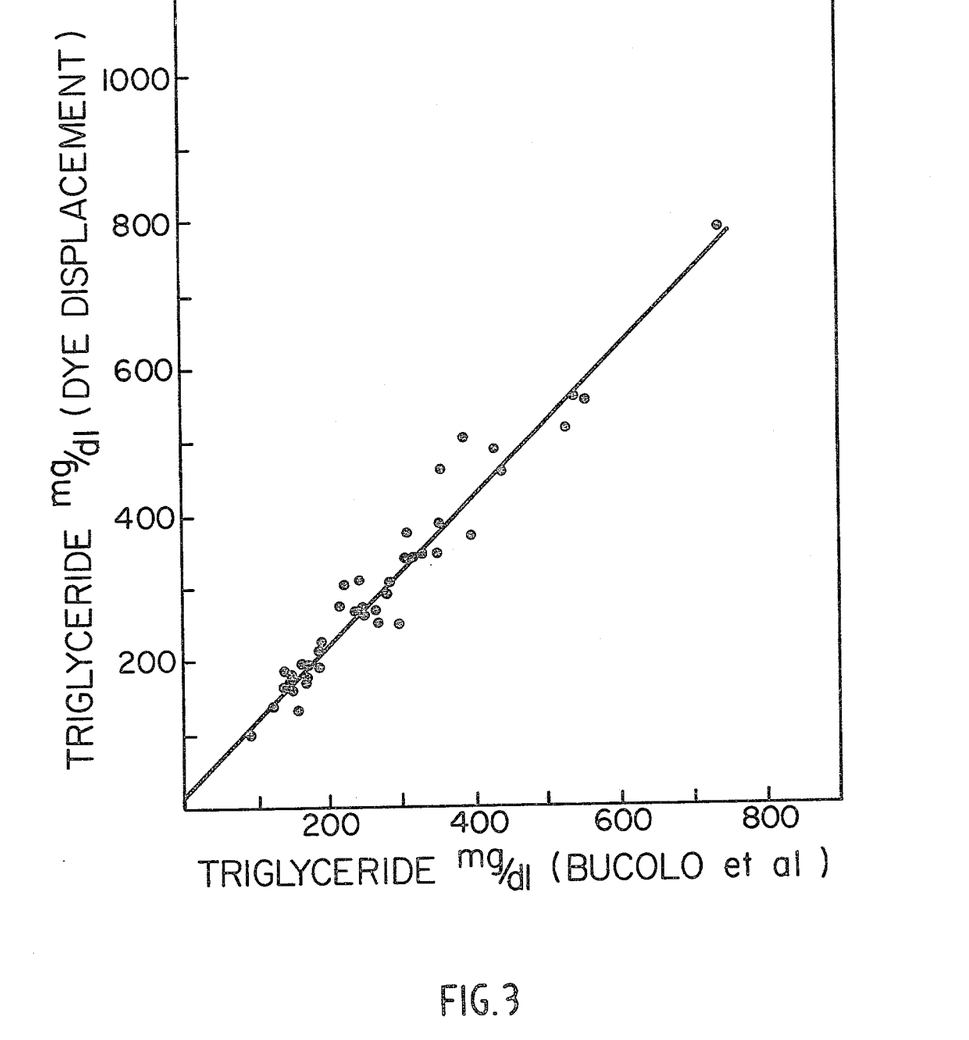
FIG. 3 correlates the triglyceride content of serum samples as determined by the technique of the present invention with that of the method disclosed in U.S. Pat. No. 3,703,591, to Bucolo et al.

Analysis of Triglycerides in Human Serum Samples Using Automated Continuous Flow Analyzer The automated analysis of triglycerides in serum samples utilized the continuous flow apparatus. (Technicon AA11). The manifold was designed to take advantage of a dual channel colorimeter so that differences in the absorbance of reagent streams containing lipase and no lipase, respectively, could be continuously monitored. Incorporation of dialyzers in the system prevented interference with the measurement caused by turbid samples. The sulfobromophthalein dye released as a result of triglyceride hydrolysis to fatty acid from the albumin-dye complex diffused across the dialyzer membrane into a recepient stream which was mixed with Na$_2$CO$_3$ to enhance the absorbance of the free dye and increase the sensitivity of the determination. The albumin-dye complex reagent described in Example 1 was used. However, with the continuous flow methodology, the reagent may be used from pH of 5.5 to 9.5 with similar results depending upon the pH optimum of the hydrolase enzyme and dye employed. The content of triglycerides in serum determined by the albumin-dye complex reagent was compared and correlated to the triglyceride content determined by the manual method of Bucolo et al in U.S. Pat. No. 3,703,591. As shown in FIG. 3 the correlation between the two procedures is excellent (r=0.984; y=1.15X−8.95), demonstrating the applicability of the new method to the analysis of triglycerides in serum.

EXAMPLE 7

Analysis of Lecithin Added to Albumin-Dye Complex Reagent by Hydrolysis with Phospholipase from Bee Venom 50 μl aliquots of ethanolic solutions of dipalmitoleyl-L-α-lecithin were added to 3.00 ml of albumin-dye complex reagent of the following composition: sodium pyrophosphate buffer, 0.10 M pH 8.0; defatted bovine serum albumin, 4.2 mg/ml and sulfobromophthalein, 0.20 mg/ml. The reagent was adjusted for linear absorbance response by the addition of 0.12 μmoles of oleic acid/ml. 650 units of phospholipase from bee venom were added and the increase in absorbance at 580 nm was measured after 30 minutes incubation at 37° C. The increase in absorbance was used to calculate the amount of lecithin hydrolyzed to fatty acid, using a standard curve such as that presented in Example 1. The recovery of lecithin was calculated on the basis of the known stoichiometry of hydrolysis of lecithin to phosphatidic acid + palmitoleic acid. As shown in Table 4 the recovery of added lecithin was between 93 and 95%.

TABLE 4

Analysis of Dipalmitoleyl Lecithin

| Lecithin Added* µmoles | Lecithin Measured | % Recovery |
|---|---|---|
| 0.21 | 0.20 | 95 |
| 0.41 | 0.38 | 93 |
| 0.82 | 0.78 | 95 |

*The amount of lecithin added was based upon analysis for organic phosphate in the preparation. (Hanahan and Jayko, Biochemical Preparations, John Wiley & Sons, Inc., New York, V4, p. 15, 1955).

EXAMPLE 8

Measurement of Triacylglycerol Hydrolase Activity

Figure 4:
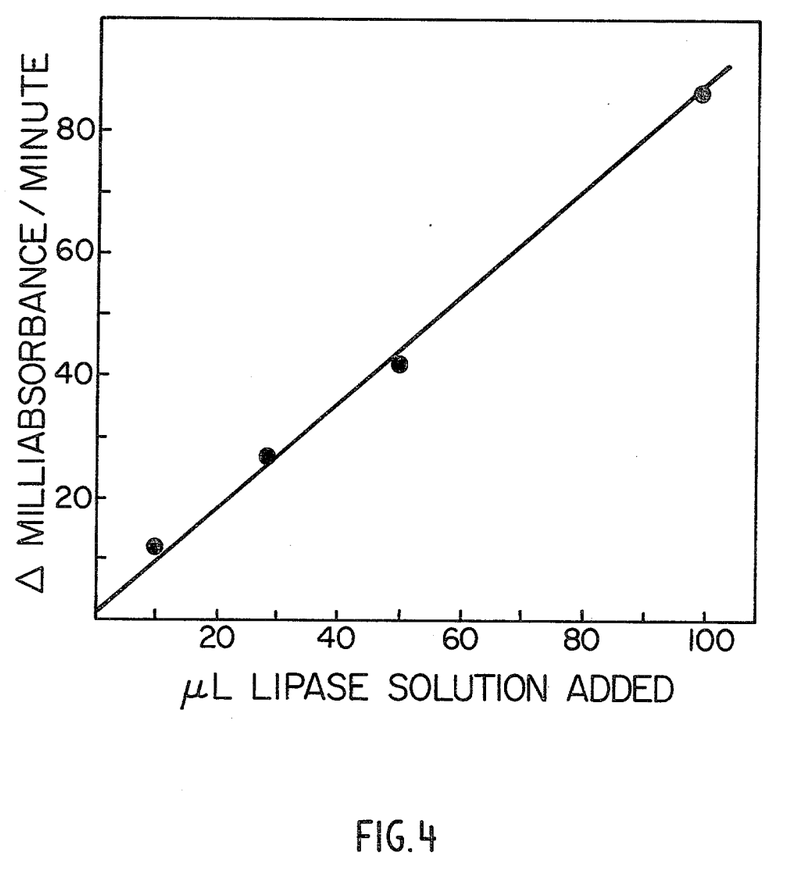
FIG. 4 illustrates the measurement of triacyl glycerol hydrolase activity.

50 µl of an isopropanol solution of triolein (3 mg/ml) were added to 3.0 ml of albumin-dye complex reagent described in Example 1. After warming to 37° C., various amounts of purified lipase from *Rizopus arrhizus* were added. The rate of change of absorbance was monitored at 580 nm during the period in which zero order kinetics was observed. As shown in FIG. 4 the rate of absorbance change was linearly proportional to the amount of lipase added.

EXAMPLE 9

Measurement of Phospholipase A Activity

Albumin-dye complex reagent was prepared with the following composition: sodium pyrophosphate buffer, 0.10 M pH 7.9, defatted bovine serum albumin, 4.2 mg/ml and sulfobromophthalein, 0.20 mg/ml. The reagent was adjusted for linear absorbance response by the addition of 0.12 µmoles of oleic acid/ml.

Figure 5:
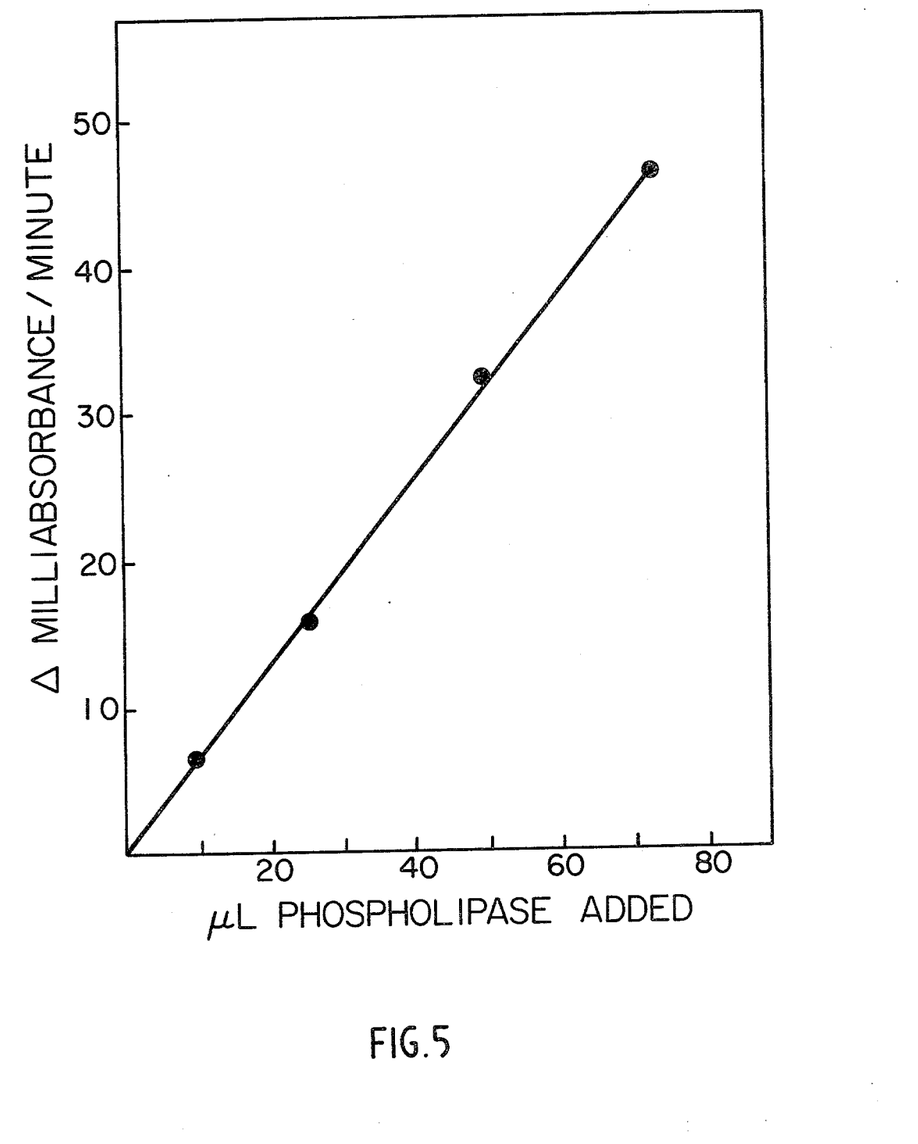
FIG. 5 illustrates the measurement of phospholipase activity by the technique of this invention.

0.20 ml of a solution of yeast lecithin, 13.1 mg/ml in H$_2$O, were added to 3.0 ml of the albumin-dye complex reagent at 37° C. Various amounts of phospholipase from bee venom were added and the rate of change in absorbance at 580 nm was monitored during the period in which zero order kinetics was observed. As shown in FIG. 5, the rate of absorbance change was linearly proportional to the amount of phospholipase added.

Having now fully described this invention, it will be apparent to one of ordinary skill in the art that many changes and modifications can be made thereto without departing from the spirit or scope of the invention set forth herein.

What is claimed as new and intended to be covered by Letters Patent is:

1. An albumin-dye complex comprising a serum or plasma albumin which contains less than 2 moles of endogenous fatty acids per mole of said serum or plasma albumin and which has been complexed with from 0.5 to 4.0 moles of a fatty acid and from 0.1 to 5.0 moles of a dye per mole of said serum or plasma albumin which dye may be displaced from said dye-albumin complex by free fatty acids.

2. The albumin-dye complex of claim 1, wherein said serum or plasma albumin is derived from sources selected from the group consisting of human, bovine, equine, rat, canine, ovine, porcine, chicken, goat and rabbit.

3. The albumin-dye complex of claim 1, wherein said serum or plasma albumin has been prepared by affinity chromatography.

4. The albumin-dye complex of claim 1, wherein said serum or plasma albumin is delipidated serum or plasma albumin.

5. The albumin-dye complex of claim 1, wherein said dye has a molar absorptivity of from $10^2$ to $10^7$.

6. The albumin-dye complex of claim 1, wherein the dye has an association constant with albumin of less than $10^8$/M.

7. The albumin-dye complex of claim 1, wherein the dye has a molar absorptivity of from $10^2$ to $10^7$ and an association constant with said albumin of from $10^3$ to $10^8$/M.

8. The albumin-dye complex of claim 1, wherein the dye is selected from the group consisting of azo dyes, sulphonphthalein dyes, triphenylmethane dyes, fluorescein dyes, naphthalenesulfonic acid dyes, anthraquinone dyes, phenoxazine dyes, tricarbocyanine dyes, indigo dyes and acridine dyes.

9. The albumin-dye complex of claim 1, wherein said albumin is bovine serum albumin, Fraction V, and said dye is sulfobromophthalein.

10. The albumin-dye complex of claim 1, wherein said albumin is selected from the group consisting of delipidated serum and delipidated plasma and said dye is sulfobromophthalein.

11. The albumin-dye complex of claim 1, wherein from 0.75 to 3.5 moles of fatty acid is present per mole of albumin.

12. An aqueous reagent comprising the albumin-dye complex of claim 1 and a buffer.

13. The aqueous reagent of claim 12, wherein the concentration of said albumin in said aqueous reagent is from $1.2 \times 10^{-4}$ M to $3.0 \times 10^{-5}$ M and a dye/albumin molar ratio of 0.16 to 8.8 to 1.

14. The aqueous reagent of claim 12, wherein the concentration of said buffer in said aqueous reagent is from 0.01 to 1.0 M.

15. The aqueous reagent of claim 12, wherein said reagent contains a hydrolase enzyme.

16. A method of determining the fatty acid content of a medium which comprises adding said medium to the aqueous reagent of claim 12 and measuring the change in absorbance of said aqueous reagent.

17. The method of claim 16, wherein said medium contains fatty acid derivatives which upon hydrolysis produce fatty acids.

18. The method of claim 17, wherein said fatty acid derivatives are hydrolyzed prior to measuring the change in absorbance of said aqueous reagent.

19. The method of claim 18, wherein said hydrolysis is an enzymatic hydrolysis.

20. A method of analyzing a medium for a fatty acid derivative which may be enzymatically converted to a fatty acid which comprises:
   (a) adding said medium to the aqueous reagent of claim 14;
   (b) measuring the absorbance of the mixture of aqueous reagent;
   (c) adding to said mixture a hydrolase enzyme which is specific for said fatty acid derivative to hydrolyze said derivative; and
   (d) subsequently measuring the absorbance of said mixture after said hydrolysis;
   wherein the difference between the first absorbance and the second absorbance is proportional to said fatty acid derivative content in said aqueous medium.

21. The method of claim 20, wherein said fatty acid derivatives are triglycerides and said hydrolase enzyme is carboxylic ester hydrolase.

22. The method of claim 20, wherein said fatty acid derivatives are cholesterol esters and said hydrolase enzyme is cholesterol esterase.

23. The method of claim 20, wherein said fatty acid derivative is lecithin and said hydrolase enzyme is phospholipase A.

24. The method of claim 20, wherein said fatty acid derivatives are ceramides and said hydrolase enzyme is ceramidase.

25. The method of claim 20, wherein said fatty acid derivative prior to enzymatic hydrolysis is enzymatically converted to a fatty acid ester or amide.

26. The method of claim 25, wherein said fatty acid derivative is selected from the group consisting of sphingomyelin, cerebrosides and gangliosides.

27. A method of analyzing blood serum for triglycerides which comprises:
  (a) admixing said blood serum with the aqueous reagent of claim 12;
  (b) measuring the absorbance of the resulting mixture;
  (c) adding to said mixture, carboxylic ester hydrolase to hydrolyze said triglycerides; and
  (d) subsequently measuring the absorbance of said mixture after said hydrolysis;
  wherein the difference between the first absorbance and the second absorbance is proportional to said triglyceride content in said serum.

28. A method of analyzing blood serum for cholesterol ester which comprises:
  (a) admixing said blood serum with aqueous reagent of claim 12;
  (b) measuring the absorbance of the resulting mixture;
  (c) adding to said mixture, cholesterol esterase to hydrolyze said cholesterol esters; and
  (d) subsequently measuring the absorbance of said mixture after said hydrolysis;
  wherein the difference between the first absorbance and the second absorbance is proportional to said cholesterol ester content in said serum.

29. A method of analyzing blood serum for lecithin which comprises:
  (a) admixing said blood serum with the aqueous reagent of claim 12;
  (b) measuring the absorbance of the resulting mixture;
  (c) adding to said mixture phospholipase A to hydrolyze said lecithin; and
  (d) subsequently measuring the absorbance of said mixture after said hydrolysis;
  wherein the difference between the first absorbance and the second absorbance is proportional to said lecithin content in said serum.

30. A method of analyzing blood serum for ceramides which comprises:
  (a) admixing said blood serum with the aqueous reagent of claim 12; p1 (b) measuring the absorbance of the resulting mixture;
  (c) adding to said mixture ceramidase to hydrolyze said ceramide; and
  (d) subsequently measuring the absorbance of said mixture after said hydrolysis;
  wherein the difference between the first absorbance and the second absorbance is proportional to said ceramide content in said serum.

31. A method of analyzing blood serum for sphingomyelin which comprises:
  (a) admixing said blood serum with the aqueous reagent of claim 12;
  (b) measuring the absorbance of the resulting mixture;
  (c) admixing with said mixture sphingomyelinase and ceramidase; and
  (d) subsequently measuring the absorbance of said mixture after said admixing;
  wherein the difference between the first absorbance and the second absorbance is proportional to said sphingomyelin content in said serum.

32. A method of analyzing blood serum for cerebrosides which comprises:
  (a) admixing said blood serum with the aqueous reagent of claim 12;
  (b) measuring the absorbance of the resulting mixture;
  (c) admixing with said mixture $\beta$-glucuronidase and ceramidase; and
  (d) subsequently measuring the absorbance of said mixture after said admixing;
  wherein the difference between the first absorbance and the second absorbance is proportional to said cerebroside content in said serum.

33. A method of analyzing blood serum for gangliosides which comprises:
  (a) admixing said blood serum with the aqueous reagent of claim 12;
  (b) measuring the absorbance of the resulting mixture;
  (c) admixing with said mixture at least one member selected from the group consisting of $\beta$-galactosidase, $\beta$-glucosidase, sialadase, and $\beta$-N-acetylhexosamidase and ceramidase; and
  (d) subsequently measuring the absorbance of said mixture;
  wherein the difference between the first absorbance and the second absorbance is proportional to said ganglioside content in said serum.

34. A method of testing a medium for hydrolase enzyme activity which comprises admixing with said medium the aqueous reagent of claim 12 and a substrate which is enzymatically hydrolyzed to fatty acids by said hydrolase enzyme and measuring the rate of change of the absorbance of said mixture, wherein said rate of change is proportional to the enzyme activity.

35. A method for analyzing a medium for fatty acid derivative which may be enzymatically converted to a fatty acid which comprises:
  (a) dividing a said medium into a first and second aliquot;
  (b) introducing one of the aliquots into the aqueous reagent of claim 12 to form a first sample;
  (c) introducing the second aliquot into the aqueous reagent of claim 12 which also contains a hydrolase enzyme which is capable of hydrolyzing said fatty acid derivatives to free fatty acid and hydrolyzing fatty acid derivative to form a second sample; and
  (d) measuring the absorbance of each of said first and second samples; wherein the difference in absorbance between said first and said second samples is proportional to the concentration of said fatty acid derivative.

36. A method of analyzing a medium for fatty acids which comprises:
  (a) measuring the fluorescence of an aqueous reagent comprising the albumin-dye complex of claim 1;
  (b) introducing into said aqueous reagent said fatty acid containing medium and measuring the fluorescence of the resulting mixture;
  wherein the change in fluorescence of said aqueous reagent is proportional to the fatty acid concentration in said medium.

* * * * *

UNITED STATES PATENT AND TRADEMARK OFFICE
CERTIFICATE OF CORRECTION

PATENT NO. : 4,195,126

DATED : March 25, 1980

INVENTOR(S) : Leo Hall

It is certified that error appears in the above—identified patent and that said Letters Patent is hereby corrected as shown below:

```
Column 1, line 17, delete "," insert --.-- after "3,679,586"
Column 1, line 62, delete "adsorption" insert --absorption--
Column 1, line 66, delete "phosphenol" insert --phosphoenol--
Column 2, line 49, after "particular" insert --there is need--
Column 3, line 52, delete "plastma" insert --plasma--
Column 3, line 65, delete "reptilliam" insert --reptilian--
Column 4, line 51, after "ricinoleic" insert --,--
Column 5, line 8, delete "billirubin" insert --bilirubin--
Column 6, line 15, delete "dye", insert --dyes--
Column 6, line 29, after "albumin" delete ","
Column 8, line 18, delete "of" insert --for--
Column 8, line 35, delete "cetylhexosaminadase" insert
--cetylhexosaminidase--
Column 9, line 16, delete "other" insert --after--; delete "in" insert
--by--
Column 9, line 57, delete "auxillary" insert --auxiliary--
Column 10, line 23, after "7" insert --,--
Column 10, line 24, delete "lyophillized" insert --lyophilized--
Column 10, line 42, delete "lambert" insert --Lambert--;
```

UNITED STATES PATENT AND TRADEMARK OFFICE
CERTIFICATE OF CORRECTION

PATENT NO. : 4,195,126
DATED : March 25, 1980
INVENTOR(S) : Leo Hall

It is certified that error appears in the above—identified patent and that said Letters Patent is hereby corrected as shown below:

Column 11, in Table 1, line 22, delete "Sehparose" insert --Sepharose--
Column 16, Claim 20, line 54, delete "14" insert --12--
Column 17, Claim 30, line 55, delete "pl"

Add the following Claims:

--37. The albumin-dye complex of Claim 2, wherein the albumin is bovine serum albumin, Fraction V.

38. The albumin-dye complex of Claim 1, wherein said serum or plasma albumin has been prepared by gel filtration.--

Figure 1, delete "adjusted reagent" and insert --unadjusted reagent--

Figure 1, delete "unadjusted reagent" and insert --adjusted reagent--.

On the Title Page after the Abstract, "36 Claims" should read -- 38 Claims --.

Signed and Sealed this

Third Day of February 1981

[SEAL]

Attest:

RENE D. TEGTMEYER

Attesting Officer    Acting Commissioner of Patents and Trademarks